(12) United States Patent
Shimura et al.

(10) Patent No.: US 12,265,187 B2
(45) Date of Patent: Apr. 1, 2025

(54) RADIATION DETECTION APPARATUS

(71) Applicant: CANON KABUSHIKI KAISHA, Tokyo (JP)

(72) Inventors: Hajime Shimura, Kanagawa (JP); Tomoyasu Soma, Kanagawa (JP); Makoto Aoki, Tokyo (JP); Motoki Tagawa, Kanagawa (JP); Hiroto Kondo, Tokyo (JP); Yutaka Ishinari, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 196 days.

(21) Appl. No.: 18/054,267

(22) Filed: Nov. 10, 2022

(65) Prior Publication Data

US 2023/0184965 A1  Jun. 15, 2023

(30) Foreign Application Priority Data

Dec. 9, 2021  (JP) ................. 2021-200401

(51) Int. Cl.
| | |
|---|---|
| *G01T 1/17* | (2006.01) |
| *H01Q 1/22* | (2006.01) |
| *H01Q 1/50* | (2006.01) |
| *H01Q 9/04* | (2006.01) |

(52) U.S. Cl.
CPC ............. *G01T 1/17* (2013.01); *H01Q 1/22* (2013.01); *H01Q 1/50* (2013.01); *H01Q 9/0421* (2013.01); *H01Q 9/045* (2013.01)

(58) Field of Classification Search
CPC ............. G01T 1/17; H01Q 1/22; H01Q 1/50
See application file for complete search history.

(56) References Cited

U.S. PATENT DOCUMENTS

| | | | |
|---|---|---|---|
| 7,495,226 B2 * | 2/2009 | Jadrich | ........ G01T 1/20 |
| | | | 250/370.09 |
| 10,061,042 B2 | 8/2018 | Suzuki | |
| 10,156,641 B2 | 12/2018 | Hiratsuka | |
| 10,721,839 B2 | 7/2020 | Tagawa | |
| 11,047,995 B2 | 6/2021 | Yagi | |

(Continued)

FOREIGN PATENT DOCUMENTS

JP  2011-112923 A  6/2011

OTHER PUBLICATIONS

U.S. Appl. No. 18/057,562, filed Nov. 21, 2022, Makoto Aoki.

*Primary Examiner* — Hugh Maupin
(74) *Attorney, Agent, or Firm* — VENABLE LLP

(57) ABSTRACT

A radiation detection apparatus includes a housing that includes an incidence surface and a back surface located on the opposite side of the incidence surface, a sensor panel that is housed in the housing and configured to convert radiation incident from the incidence surface into an electrical signal, a conductive plate that is housed in the housing and extends in a direction intersecting with a normal to the incidence surface, and an antenna element housed in the housing. The conductive plate is located between the sensor panel and the back surface. The antenna element is located between the conductive plate and the back surface. The antenna element includes a portion that extends in the direction intersecting with the normal to the incidence surface. The conductive plate is configured to function as a ground for the antenna element.

12 Claims, 6 Drawing Sheets

(56) References Cited

U.S. PATENT DOCUMENTS

| | | | |
|---|---|---|---|
| 11,128,820 B2 | 9/2021 | Tamura | |
| 11,224,390 B2 | 1/2022 | Tagawa | |
| 11,320,546 B2 | 5/2022 | Kondo | |
| 2007/0272873 A1* | 11/2007 | Jadrich | G01T 1/20 |
| | | | 250/370.11 |
| 2012/0228499 A1 | 9/2012 | Koyanagi | |
| 2013/0099126 A1* | 4/2013 | Iwata | G01T 1/20184 |
| | | | 250/366 |
| 2017/0299735 A1* | 10/2017 | MacLaughlin | G01T 7/00 |
| 2017/0346323 A1* | 11/2017 | MacLaughlin | A61B 6/4233 |
| 2018/0110495 A1* | 4/2018 | MacLaughlin | A61B 6/545 |
| 2020/0064501 A1* | 2/2020 | Jadrich | G01T 1/2002 |
| 2021/0011176 A1 | 1/2021 | Ishinari | |
| 2022/0196859 A1 | 6/2022 | Fujiyoshi | |
| 2022/0247927 A1 | 8/2022 | Kida | |
| 2022/0263236 A1* | 8/2022 | Aoki | H01Q 9/26 |
| 2023/0089687 A1* | 3/2023 | Kwon | H01Q 1/38 |
| | | | 343/702 |

* cited by examiner

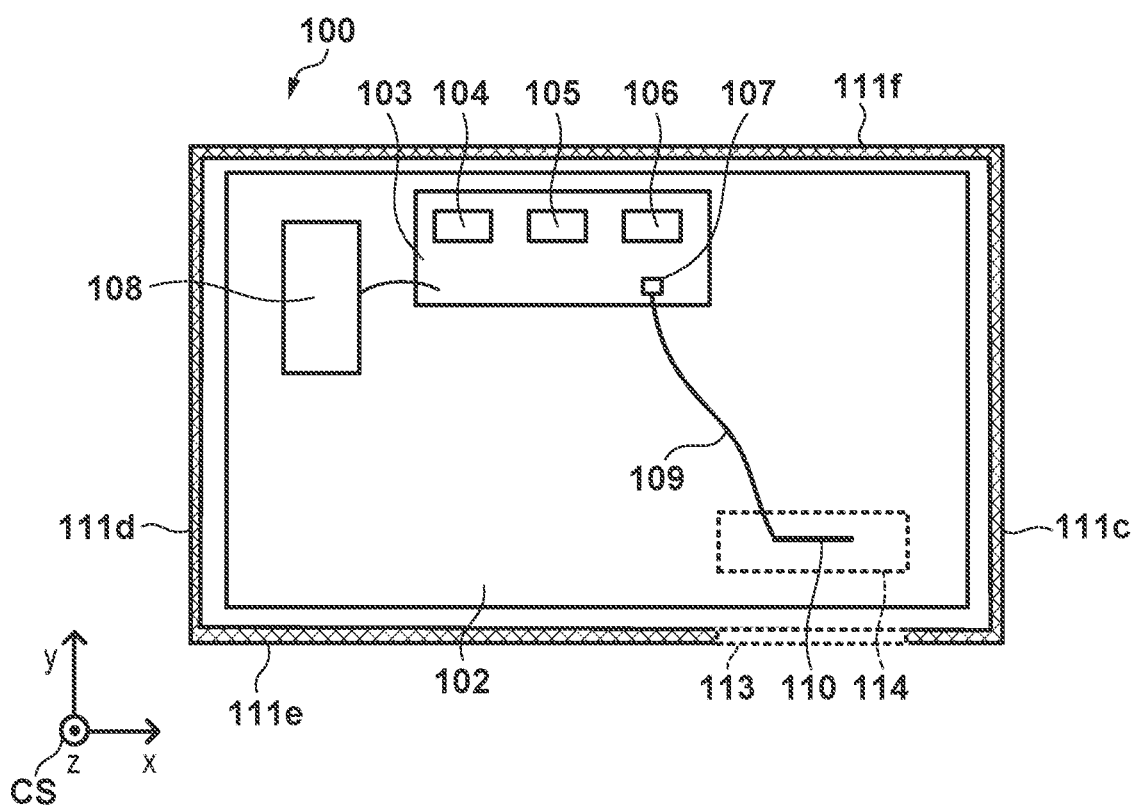

RADIATION DETECTION APPARATUS

BACKGROUND OF THE INVENTION

Field of the Invention

The present invention relates to a radiation detection apparatus.

Description of the Related Art

Many digital radiography apparatuses have been productized as thin and light portable radiography apparatuses. To improve portability, Japanese Patent Laid-Open No. 2011-112923 suggests a wireless radiography apparatus that performs wireless communication with an external apparatus. There is a desire to reduce the thickness of a radiation detection apparatus to make the radiation detection apparatus easy to handle. The Japanese Industrial Standards (JIS) also define a standard thickness of a radiography apparatus, and it is not appropriate to exceed this thickness. However, depending on the antenna configuration for performing wireless communication, there is a possibility that the thickness of a radiation detection apparatus is increased, or sufficient antenna characteristics cannot be attained.

SUMMARY OF THE INVENTION

In some aspects of the present invention, an appropriate antenna configuration for a radiation detection apparatus is provided. In an embodiment, a radiation detection apparatus is provided. The radiation detection apparatus includes a housing that includes an incidence surface and a back surface located on the opposite side of the incidence surface, a sensor panel that is housed in the housing and configured to convert radiation incident from the incidence surface into an electrical signal, a conductive plate that is housed in the housing and extends in a direction intersecting with a normal to the incidence surface, and an antenna element housed in the housing. The conductive plate is located between the sensor panel and the back surface. The antenna element is located between the conductive plate and the back surface. The antenna element includes a portion that extends in the direction intersecting with the normal to the incidence surface. The conductive plate is configured to function as a ground for the antenna element.

Further features of the present invention will become apparent from the following description of exemplary embodiments with reference to the attached drawings.

BRIEF DESCRIPTION OF THE DRAWINGS

FIG. 1A to FIG. 1C are schematic diagrams for describing an exemplary configuration of a radiation detection apparatus according to a first embodiment.

DESCRIPTION OF THE EMBODIMENTS

Figure 1A:
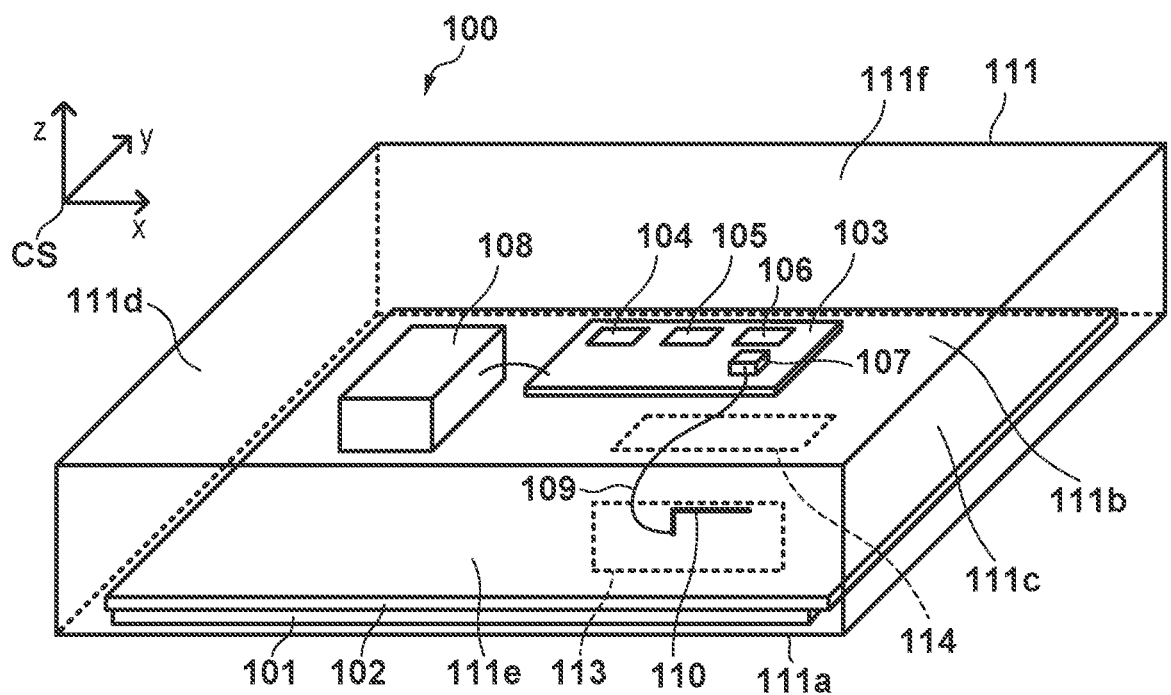

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

First Embodiment

Figure 1B:
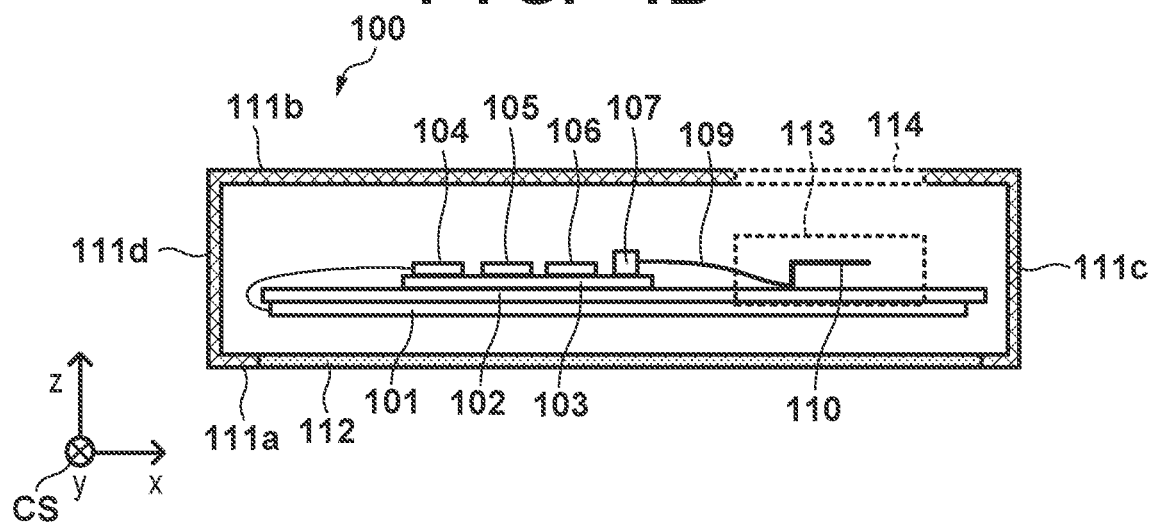

An exemplary configuration of a radiation detection apparatus 100 according to a first embodiment will be described with reference to FIG. 1A to FIG. 1C. The radiation detection apparatus 100 has a function of detecting incident radiation. In a case where the radiation detection apparatus 100 is used to generate a radiation image, the radiation detection apparatus 100 may be referred to as a radiography apparatus. FIG. 1A shows a perspective view of the radiation detection apparatus 100. In FIG. 1A, a housing 111 is illustrated only by its outline so as to make the internal structure of the housing 111 viewable. However, the housing 111 may be formed by an opaque material. FIG. 1B shows a lateral cross-sectional view of the radiation detection apparatus 100. FIG. 1C shows a plan cross-sectional view of the radiation detection apparatus 100. A three-dimensional Cartesian coordinate system CS is set to show the directions of the radiation detection apparatus 100. In the following description, the axes in the Cartesian coordinate system CS will be intended in a case where the x-axis, the y-axis, and the z-axis are referred to.

The radiation detection apparatus 100 includes, for example, a sensor panel 101, a sensor support plate 102, a printed circuit board 103, a battery 108, a coaxial cable 109, an antenna element 110, and the housing 111. The sensor panel 101, sensor support plate 102, printed circuit board 103, battery 108, coaxial cable 109, and antenna element 110 are housed in the housing 111. The housing 111 defines the external appearance of the radiation detection apparatus 100.

The housing 111 may be in a thin cuboid shape. A thin cuboid may mean that, for example, among the lengths of three edges that gather at one vertex, the length of the shortest edge is sufficiently smaller than (e.g., not more than one-tenth of, or not more than one-fifth of) the lengths of other two edges. Also, the housing 111 being in a cuboid shape may mean that the housing 111 has a shape of a cuboid or a shape similar to that. For example, the six surfaces of the housing 111 may be flat, may have differences in level (including projected portions and recessed portions), or may be curved surfaces. In any case, the housing 111 will be described to be in a cuboid shape. As the housing 111 defines the external appearance of the radiation detection apparatus 100, the radiation detection apparatus 100, too, is in a thin cuboid shape.

Among the six surfaces of the housing 111, a surface that faces a radiation source during the use of the radiation detection apparatus 100 is referred to as an incidence surface 111a. In the example of FIG. 1A, the lower surface of the housing 111 is the incidence surface 111a. That is to say, radiation is emitted toward the radiation detection apparatus 100 from the lower side of FIG. 1A. Radiation that has been emitted from the radiation source and transmitted through a subject is made incident on the incidence surface 111a and reaches the inside (specifically, the sensor panel 101) of the radiation detection apparatus 100. Among the six surfaces of the housing 111, a surface located on the opposite side of the incidence surface 111a is referred to as a back surface 111b. The incidence surface 111a and the back surface 111b are both parallel to the xy plane.

Among the six surfaces of the housing 111, four surfaces other than the incidence surface 111a and the back surface 111b are referred to as side surfaces 111c to 111f. The side surface 111c and the side surface 111d are on the opposite side of each other, and they are both parallel to the yz plane. The side surface 111e and the side surface 111f are on the opposite side of each other, and they are both parallel to the xz plane.

The housing 111 is formed by a stiff material, except for the regions that will be described below. Such a material may be a conductive material. For example, the housing 111 may be formed by a metal, such as magnesium, stainless, aluminum, copper, and iron. The housing 111 may be formed by a resin with a metallic mesh embedded therein. The housing 111 may be formed by a conductive resin, such as Carbon Fiber Reinforced Plastics (CFRP). A part of the incidence surface 111a (e.g., a portion 112 that overlaps the sensor panel 101 in a plan view relative to the incidence surface 111a (the z-axis direction)) may be formed by a material that has a higher radiation transmittance than a region surrounding it. Also, the housing 111 may include a radio wave transmissive region 113 in a part of the side surface 111e, and a radio wave transmissive region 114 in a part of the back surface 111b. The details of the radio wave transmissive regions 113 and 114 will be described later.

The sensor panel 101 converts radiation that has been incident on the radiation detection apparatus 100 from the incidence surface 111b into electrical signals. A plurality of pixel circuits are arranged two-dimensionally in the sensor panel 101. Each pixel circuit includes a conversion element for converting radiation into a charge, and a switch element for transferring an electrical signal corresponding the amount of charge. The sensor panel 101 is installed inside the housing 111 so as to be substantially parallel to the incidence surface 111a. The state where two planes are substantially parallel to each other includes not only a case where the two planes are parallel to each other (i.e., the angle formed by the normals to the two planes is 0 degrees), but also a case where the two planes are almost parallel to each other (e.g., the angle formed by the normals to the two planes is equal to or smaller than 5 degrees, or equal to or smaller than 10 degrees).

The sensor panel 101 is supported by the sensor support plate 102. The sensor support plate 102 is installed inside the housing 111 so as to be substantially parallel to the incidence surface 111a. Also, the sensor support plate 102 is substantially parallel to the sensor panel 101 as well. For example, the sensor support plate 102 may be attached to the housing 111. The sensor support plate 102 may be formed by a conductive material. For example, similarly to the housing 111, the sensor support plate 102 may be formed by a metal, may be formed by a resin with a metallic mesh embedded therein, or may be formed by a conductive resin, such as CFRP. In a case where the sensor support plate 102 is conductive, the sensor support plate 102 may also be referred to as a conductive plate.

The sensor panel 101 may be attached directly to the sensor support plate 102 (i.e., the sensor panel 101 may be in contact with the sensor support plate 102). Alternatively, a radiation shield plate (not shown) may be arranged between the sensor panel 101 and the sensor support plate 102. The radiation shield plate can protect the circuits of the printed circuit board 103 from radiation that has been incident on the radiation detection apparatus 100, and suppress image deterioration caused by backscattering of radiation. The sensor support plate 102 is located on the opposite side from the incidence surface 111a relative to the sensor panel 101. In other words, the sensor support plate 102 is located between the sensor panel 101 and the back surface 111b. In a plan view relative to the incidence surface 111a, the sensor support plate 102 may be larger than the sensor panel 101, may have the same size thereas, or may be smaller than the sensor panel 101.

The printed circuit board 103, battery 108, and antenna element 110 are attached to the sensor support plate 102 (specifically, a surface thereof near the back surface 111b). Various circuits and components for realizing the operations of the radiation detection apparatus 100 are installed on the printed circuit board 103. For example, a readout circuit 104, a control circuit 105, a wireless communication circuit 106, and a connector 107 are mounted on the printed circuit board 103. Each of the readout circuit 104, control circuit 105, and wireless communication circuit 106 may be an integrated circuit (IC). The readout circuit 104 is configured to read out electrical signals from the pixel circuits of the sensor panel 101. The control circuit 105 is configured to perform overall control on the radiation detection apparatus 100. The wireless communication circuit 106 is configured to perform wireless communication between the radiation detection apparatus 100 and an external apparatus with use of the antenna element 110. The external apparatus denotes an apparatus that is situated outside the radiation detection apparatus 100. The battery 108 supplies operating power to each constituent element of the radiation detection apparatus 100. Alternatively, the wireless communication circuit 106 and the connector 107 may be mounted on the printed circuit board 103, and the wireless communication circuit 106 and the connector 107 may be mounted on another different printed circuit board.

The antenna element 110 and the connector 107 are connected to each other by the coaxial cable 109. The coaxial cable 109 functions as a feed line of an antenna composed of the antenna element 110. The coaxial cable 109 includes a first conductor and a second conductor that are electrically separated from each other. For example, the coaxial cable 109 includes an inner conductor (also referred to as a core) and an outer conductor (also referred to as an outer sheath), and these conductors are electrically separated from each other. The state where two members are electrically separated from each other may mean that these members do not compose the same node in an equivalent circuit diagram. On the other hand, the state where two members are electrically connected to each other may mean that these members compose the same node in an equivalent circuit diagram.

The wireless communication circuit 106 supplies electrical signals corresponding to data signals to be wirelessly transmitted to the antenna element 110 via the connector 107 and the coaxial cable 109. The antenna element 110 radiates radio waves corresponding to the supplied electrical signals. For example, the antenna element 110 may be used to wirelessly transmit image signals generated by the radiation detection apparatus 100. Furthermore, the antenna element 110 may be used to receive radio waves including signals from an external apparatus. In this way, the antenna element 110 is used for wireless communication with an external apparatus.

The antenna element 110 is configured to transmit/receive radio waves of a specific operating frequency. The operating frequency may be a frequency that is appropriate for transmission/reception by the antenna element 110 (e.g., with a large gain). The antenna element 110 may use any frequency included in a frequency band of a specific range as the operating frequency. In this case, this frequency band of the specific range may be referred to as an operating frequency band. The antenna element 110 may use a plurality of frequency bands as operating frequency bands.

For example, assume that the antenna element 110 is a dual-band antenna used in wireless communication that conforms with the standards of a wireless LAN (IEEE 802.11a/b/g/n/ac). In this case, both of the 2.4 GHz band and the 5 GHz band are the operating frequency bands of the antenna element 110. Assume that the antenna element 110 is a single-band antenna used in wireless communication that conforms with the standards of a wireless LAN (IEEE 802.11b/g/n). In this case, the 2.4 GHz band is the operating frequency band of the antenna element 110. Assume that the antenna element 110 is a single-band antenna used in wireless communication that conforms with the standards of a wireless LAN (IEEE 802.11a/n/ac). In this case, the 5 GHz band is the operating frequency band of the antenna element 110. Assume that the antenna element 110 is a tri-band antenna used by a wireless communication function that conforms with the standards of a wireless LAN (IEEE 802.11a/b/g/n/ac/ax/be). In this case, the 2.4 GHz band, the 5 GHz band, and the 6 GHz band are the operating frequency bands of the antenna element 110. The operating frequency band of the antenna element 110 may be a band other than the ones described above.

Radio waves radiated by the antenna element 110 propagates to the outside of the housing 111 via the radio wave transmissive regions 113 and 114. Also, radio waves from an external apparatus propagates to the inside of the housing 111 via the radio wave transmissive regions 113 and 114. Although the following describes the radio wave transmissive region 113, a similar description applies to the radio wave transmissive region 114 as well. The radio wave transmissive region 113 denotes a region that has a higher radio wave transmittance than a conductor region around the radio wave transmissive region 113 in the housing 111. For example, the radio wave transmissive region 113 may be formed by removing a part of the housing 111 formed by a conductor material. That is to say, the radio wave transmissive region 113 does not include a conductive material. The radio wave transmissive region 113 includes a portion that has a width equal to or larger than one-half of the wavelength of the operating frequency of the antenna element 110. For example, in a case where the radio wave transmissive region 113 has a rectangular shape, at least the long sides thereof are equal to or larger than one-half of the wavelength of the operating frequency of the antenna element 110. In a case where the antenna element 110 has a plurality of operating frequencies, the radio wave transmissive region 113 includes a portion that has a width equal to or larger than one-half of the wavelength of the lowest operating frequency of the antenna element 110. The antenna element 110 is located closer to the side surface 111$e$ than to the side surface 111$f$. For this reason, the radio wave transmissive region 113 is formed on the side surface 111$e$ rather than on the side surface 111$f$.

The radio wave transmissive region 113 may be covered by an insulating cover. This cover may have a light-blocking property to suppress exposure of the sensor panel 101 to external light. For example, the cover may be formed by a resin. The locations and the numbers of the radio wave transmissive regions 113 and 114 are not limited to the aforementioned example. The housing 111 may include another radio wave transmissive region, in place of or in addition to the radio wave transmissive region 113 and the radio wave transmissive region 114. For example, the housing 111 may include another radio wave transmissive region on the side surface 111$c$.

Figure 2A:
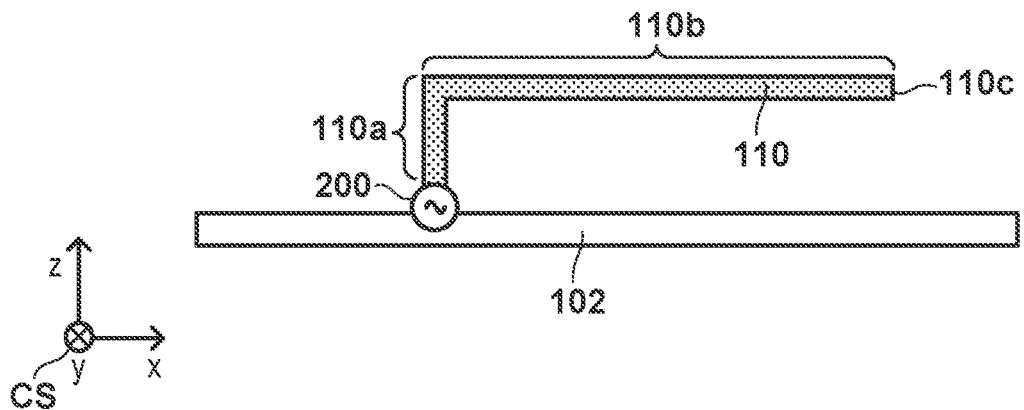
FIG. 2A to FIG. 2C are schematic diagrams for describing an exemplary configuration of an antenna element according to the first embodiment.
Figure 2B:
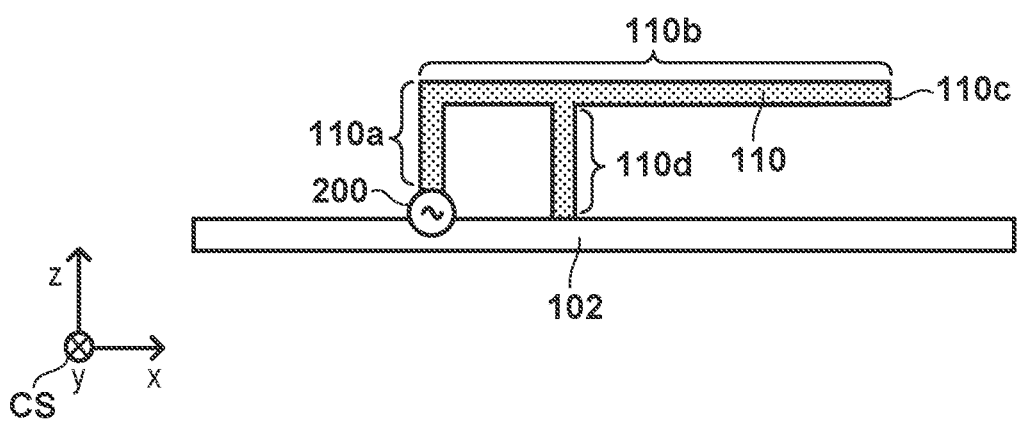
Figure 2C:
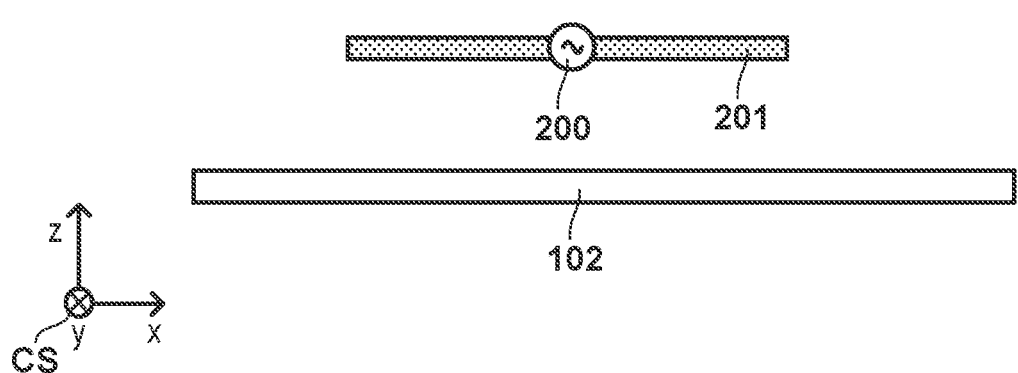

A specific configuration of the antenna element 110 will be described with reference to FIG. 2A to FIG. 2C. FIG. 2A illustrates a case where the antenna element 110 is an inverted-L antenna. FIG. 2B illustrates a case where the antenna element 110 is an inverted-F antenna. FIG. 2C illustrates a case where a dipole antenna 201 is used in place of the antenna element 110, as a comparative example. The antenna element 110 may be, for example, a conductive member formed by a metal, such as iron. The antenna element 110 may have a rod-like shape with a circular or square cross-section, or may have a plate-like shape with a rectangular cross-section.

Among both ends of the coaxial cable 109, an end portion that is different from an end portion connected to the connector 107 functions as a feed point 200. The feed point 200 denotes a position at which power is supplied to the antenna composed of the antenna element 110. Specifically, at the feed point 200, the inner conductor of the coaxial cable 109 is electrically and physically connected to one end of the antenna element 110. Electrical signals are supplied from the printed circuit board 103 to the antenna element 110 via the inner conductor of the coaxial cable 109. Also, at the feed point 200, the outer conductor of the coaxial cable 109 is electrically and physically connected to the sensor support plate 102. The ground potential is supplied from the printed circuit board 103 to the sensor support plate 102 via the outer conductor of the coaxial cable 109. The ground potential may be supplied to the sensor support plate 102 at a position different from the feed point 200.

The sensor support plate 102 is conductive, and has a sufficient size relative to the wavelength of the operating frequency of the antenna element 110 (e.g., a width equal to or larger than one-fourth of this wavelength). Therefore, the sensor support plate 102 functions as a ground for the antenna element 110. That is to say, the antenna is composed of the antenna element 110 and the sensor support plate 102.

As shown in FIG. 2A, the inverted-L antenna is composed of the antenna element 110 and the sensor support plate 102. The inverted-L antenna denotes a monopole antenna having a conductive member that is bent halfway. Specifically, the antenna element 110 includes a near-side portion 110$a$ and a far-side portion 110$b$ that are perpendicular to each other. The near-side portion 110$a$ extends from the feed point 200 in the positive direction along the z axis (i.e., the direction that is perpendicular to the incidence surface 111$a$ and approaches the back surface 111$b$). The far-side portion 110$b$ extends from an end portion of the near-side portion 110$a$ that is on the opposite side of the feed point 200, in the positive direction along the x axis (i.e., the direction that is parallel to the sensor panel 101 and approaches the side surface 111$c$). Although the far-side portion 110$b$ extends in the direction that approaches the side surface 111$c$ in the present example, it may extend in another direction. An end portion of the far-side portion 110$b$ that is far from the feed point 200 is referred to as an open end 110$c$.

By using the inverted-L antenna as the antenna element 110 as shown in FIG. 2A, the height of the antenna element 110 (i.e., the width thereof in the z-axis direction) can be reduced compared to a case where a monopole antenna extending in a straight line in a normal direction of the incidence surface 111a is used. Therefore, the thickness of the radiation detection apparatus 100 (i.e., the width thereof in the z-axis direction) can also be reduced.

As shown in FIG. 2B, the antenna element 110 may compose an inverted-F antenna. Specifically, the antenna element 110 includes a short-circuit portion 110d in addition to the near-side portion 110a and the far-side portion 110b described in FIG. 2A. One end of the short-circuit portion 110d is physically and electrically connected to the far-side portion 110b, whereas the other end of the short-circuit portion 110d is physically and electrically connected to the sensor support plate 102.

A description is now given of the case of FIG. 2C where the dipole antenna 201 is used as the antenna of the radiation detection apparatus 100, as a comparative example. In this case, the sensor support plate 102 does not function as a ground for the dipole antenna 201. Therefore, if the distance between the dipole antenna 201 and the sensor support plate 102 is short, the operating frequency of the dipole antenna 201 changes. In order to reduce such an influence, it is necessary for the dipole antenna 201 and the sensor support plate 102 to be separated from each other by a certain distance. For this reason, it is difficult to reduce the thickness of the radiation detection apparatus 100 compared to the configuration of the antenna element 110 according to the present embodiment.

The foregoing has described the embodiment in relation to a case where the antenna element 110 is an inverted-L antenna or an inverted-F antenna. The antenna element 110 may compose another type of antenna for which the sensor support plate 102 operates as a ground.

In the foregoing example, the far-side portion 110b of the antenna element 110 extends in the direction perpendicular to a normal to the incidence surface 111a (i.e., the direction parallel to the incidence surface 111a). Alternatively, the far-side portion 110b of the antenna element 110 may extend in another direction that intersects with a normal to the incidence surface 111a. For example, the far-side portion 110b of the antenna element 110 may extend in the direction that is substantially parallel to the incidence surface 111a. Furthermore, the far-side portion 110b of the antenna element 110 may extend in the direction that, together with a normal to the incidence surface 111a, forms an angle equal to or larger than 30 degrees, equal to or larger than 45 degrees, or equal to or larger than 60 degrees. No matter which direction it extends, the height of the antenna element 110 can be reduced compared to a case where a monopole antenna extending in a straight line in a normal direction of the incidence surface 111a is used. In addition, the antenna element 110 may be a straight conductive member which is not bent halfway and which extends in the direction that intersects with a normal to the incidence surface 111a. In this case, too, the height of the antenna element 110 can be reduced.

In the foregoing example, the sensor support plate 102 extends in the direction perpendicular to a normal to the incidence surface 111a (i.e., the direction parallel to the incidence surface 111a). Alternatively, the sensor support plate 102 may extend in another direction that intersects with a normal to the incidence surface 111a. For example, the sensor support plate 102 may extend in the direction that is substantially parallel to the incidence surface 111a.

Figure 3A:
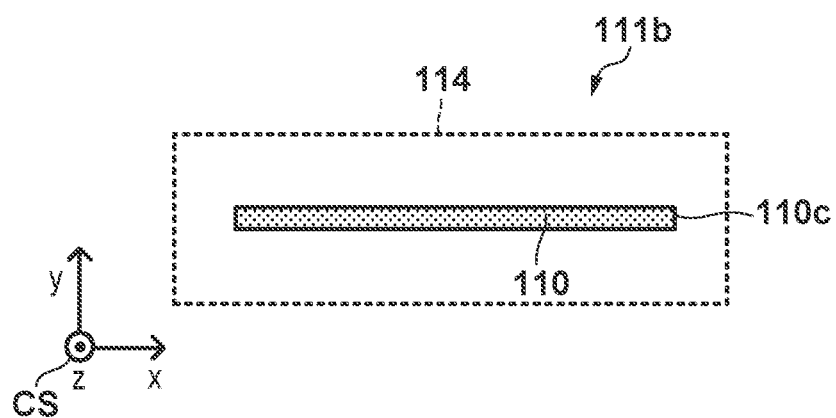
FIG. 3A and FIG. 3B are schematic diagrams for describing a positional relationship between the antenna element and a radio wave transmissive region according to the first embodiment.

Next, the positional relationship between the radio wave transmissive region 114 and the antenna element 110 will be described with reference to FIG. 3A and FIG. 3B. Although the following describes the positional relationship between the radio wave transmissive region 114 and the antenna element 110, the same may go for the positional relationship between the radio wave transmissive region 113 and the antenna element 110. The back surface 111b of the housing 111 is formed by a conductor, except for the radio wave transmissive region 114. A region formed by such a conductor, namely a conductor region, does not allow radio waves radiated by the antenna element 110 to be transmitted therethrough. On the other hand, the radio wave transmissive region 114 allows radio waves radiated by the antenna element 110 to be transmitted therethrough. In view of this, in some embodiments, the antenna element 110 is arranged in such a manner that it does not overlap the conductor region of the back surface 111b, but overlaps only the radio wave transmissive region 114, in a plan view relative to the radio wave transmissive region 114 (i.e., in the z-axis direction) as shown in FIG. 3A. In other words, the antenna element 110 fits in the radio wave transmissive region 114 in a plan view relative to the radio wave transmissive region 114. With this arrangement, the amount of energy of radio waves that are radiated by the antenna element 110 and transmitted through the radio wave transmissive region 114 is maximized, thereby enabling the radio waves to be radiated efficiently to the outside of the housing 111. For example, the antenna element 110 and the radio wave transmissive region 114 may be arranged in such a manner that the center of the antenna element 110 and the center of the radio wave transmissive region 114 overlap each other in a plan view relative to the radio wave transmissive region 114. The antenna element 110 and the radio wave transmissive region 114 may be arranged in such a manner that the antenna element 110 extends in the lengthwise direction of the radio wave transmissive region 114 (the x-axis direction).

Figure 3B:
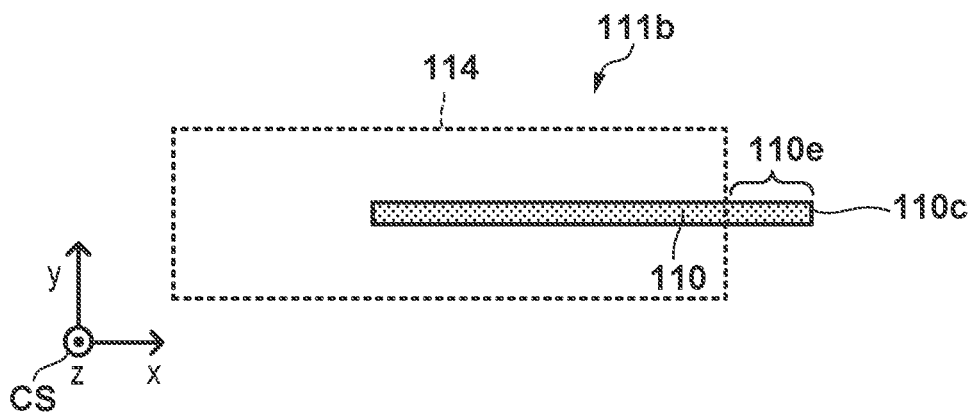

In the embodiment shown in FIG. 3B, one portion of the antenna element 110 is arranged so as to overlap the conductor region of the back surface 111b, whereas the other portion of the antenna element 110 is arranged so as to overlap the radio wave transmissive region 114, in a plan view relative to the radio wave transmissive region 114 (i.e., in the z-axis direction). The portion that overlaps the conductor region of the back surface 111b is referred to as an overlap portion 110e. In other words, the antenna element 110 does not fit in the radio wave transmissive region 114 and protrudes outside the radio wave transmissive region 114 in a plan view relative to the back surface 111b. The overlap portion 110e includes the open end 110c.

In some cases, the operating frequency band of the antenna may not fall within a desired range depending on the positional relationships between the antenna element 110 and other constituent elements (e.g., the housing 111, components on the printed circuit board 103, and so on). The distance between the overlap portion 110e and a conductor portion of the housing 111 is reduced by adjusting the position of the radio wave transmissive region 114 so that the antenna element 110 includes the overlap portion 110e. As a result, more intense electromagnetic coupling is achieved between the antenna element 110 and the conductive portion of the housing 111, thereby causing the operating frequency band of the antenna to change. In this way, simply by changing the position of the radio wave transmissive region 114, the operating frequency band of the antenna can be adjusted without changing the configurations of the constituent elements inside the housing 111.

Second Embodiment

Figure 4A:
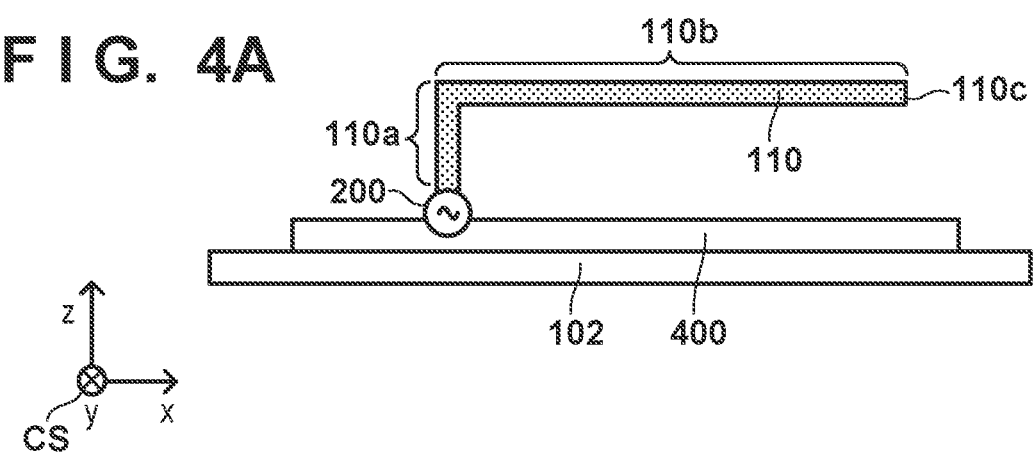
FIG. 4A to FIG. 4C are schematic diagrams for describing an exemplary configuration of a radiation detection apparatus according to a second embodiment and a third embodiment.

A configuration of a radiation detection apparatus 100 according to a second embodiment will be described with reference to FIG. 4A. The following description focuses on the differences from the first embodiment. A description of the contents that may be similar to those of the first embodiment will be omitted. Various exemplary modifications that have been described in connection with the first embodiment are applicable to the second embodiment as well.

The radiation detection apparatus 100 according to the second embodiment differs from the first embodiment in that it further includes a conductive plate 400 between an antenna element 110 and a sensor support plate 102. It can also be said that the conductive plate 400 is located between the sensor support plate 102 and a back surface 111b. Furthermore, the antenna element 110 is located between the conductive plate 400 and the back surface 111b.

The conductive plate 400 is electrically connected to the sensor support plate 102. The conductive plate 400 may be in contact with the sensor support plate 102, or may be coupled thereto via another conductive material (e.g., a conductive adhesive tape). An outer conductor of a coaxial cable 109 is physically and electrically connected to the conductive plate 400 at a feed point 200. That is to say, the ground potential is supplied from a printed circuit board 103 to the conductive plate 400 via the outer conductor of the coaxial cable 109. The conductive plate 400 functions as a ground for the antenna element 110. Specifically, the conductive plate 400 has a sufficient size relative to the wavelength of the operating frequency of the antenna element 110 (e.g., a width equal to or larger than one-fourth of this wavelength). As the sensor support plate 102 is electrically connected to the conductive plate 400, the sensor support plate 102, too, functions as a ground for the antenna element 110. That is to say, the conductive plate 400 and the sensor support plate 102 jointly function as a ground for the antenna element 110.

The conductive plate 400 may be smaller than the sensor support plate 102 in a plan view relative to an incidence surface 111a (the z-axis direction). Also, the conductive plate 400 may be larger than the antenna element 110 in a plan view relative to the incidence surface 111a.

In the foregoing example, the conductive plate 400 extends in the direction perpendicular to a normal to the incidence surface 111a (i.e., the direction parallel to the incidence surface 111a). Alternatively, the conductive plate 400 may extend in another direction that intersects with a normal to the incidence surface 111a. For example, the sensor support plate 102 may extend in the direction that is substantially parallel to the incidence surface 111a.

Furthermore, in the foregoing example, the antenna element 110 and the conductive plate 400 are members that are distinct from each other. Alternatively, the antenna element 110 and the conductive plate 400 may be integrally formed and configured as an antenna element (referred to as an antenna element A). Especially, in a case where the antenna element A is an inverted-F antenna shown in FIG. 2B, it includes a short-circuit portion 110d in addition to a near-side portion 110a and a far-side portion 110b. Therefore, the antenna element 110 and the conductive plate 400 may be integrally formed by connecting the antenna element 110 and the conductive plate 400 via the short-circuit portion 110d. In this case, a conductive plate that has a configuration and advantageous effects similar to those of the aforementioned conductive plate 400 (referred to as a conductive plate A) may be further provided between the antenna element A and the sensor support plate 102.

In this case, the antenna element A may be in contact with the conductive plate A, or may be coupled thereto via another conductive member (e.g., a conductive adhesive tape). The conductive plate A may be in contact with the sensor support plate 102, or may be coupled thereto via another conductive material (e.g., a conductive adhesive tape).

Third Embodiment

Figure 4B:
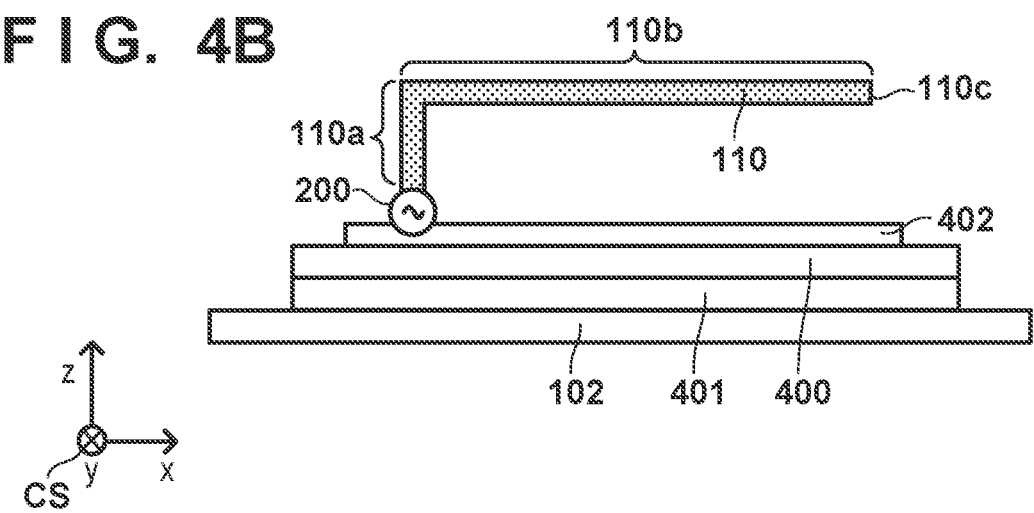

A configuration of a radiation detection apparatus 100 according to a third embodiment will be described with reference to FIG. 4B. The following description focuses on the differences from the first embodiment. A description of the contents that may be similar to those of the first embodiment will be omitted. Various exemplary modifications that have been described in connection with the first embodiment are applicable to the third embodiment as well.

The radiation detection apparatus 100 according to the third embodiment differs from the first embodiment in that it further includes a conductive plate 400, an insulating member 401, and a conductive member 402 between an antenna element 110 and a sensor support plate 102. The conductive member 402 has an adhesive function, and causes the antenna element 110 and the conductive plate 400 to be coupled to each other. The conductive member 402 may be, for example, a conductive double-sided tape.

The conductive plate 400 may be similar in size to that of the second embodiment. Furthermore, the ground potential may be supplied from a printed circuit board 103 to the conductive plate 400 via an outer conductor of a coaxial cable 109. Therefore, the conductive plate 400 functions as a ground for the antenna element 110.

The insulating member 401 has an adhesive function, and causes the conductive plate 400 and the sensor support plate 102 to be coupled to each other. The insulating member 401 may be, for example, an insulating double-sided tape. The insulating member 401 causes the conductive plate 400 and the sensor support plate 102 to be electrically separated from each other. The insulating member 401 is located between the conductive plate 400 and the sensor support plate 102.

Figure 4C:
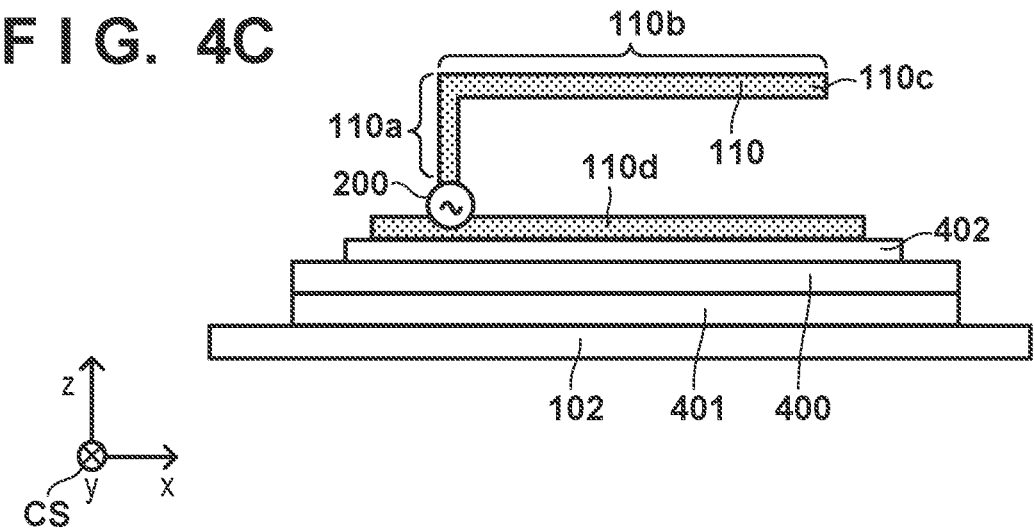

Another configuration of the radiation detection apparatus 100 according to the third embodiment will be described with reference to FIG. 4C. The following description focuses on the differences from FIG. 4B. The antenna element 110 differs from FIG. 4B in that it further includes a conductive plate 110d. In the antenna element 110, the plurality of portions 110a, 110b, 110c, and 110d are integrally formed. In this case, the antenna element 110 may be an inverted-F antenna. The conductive member 402 has an adhesive function, and causes the antenna element 110 (specifically, the conductive plate 110d thereof) and the conductive plate 400 to be coupled to each other. The conductive member 402 may be, for example, a conductive double-sided tape. The conductive plate 110d of the antenna element 110 may be larger than the far-side portion 110b of the antenna element 110 in a plan view relative to an incidence surface 111a. Also, the conductive plate 400 may be larger than the conductive plate 110d of the antenna element 110 in a plan view relative to the incidence surface 111a. Furthermore, the ground potential may be supplied from the printed circuit board 103 to the conductive plate 110d of the antenna element 110 via the outer conductor of the coaxial cable 109. Therefore, the conductive plate 400, which is coupled to and is also electrically connected to the conductive plate 110d, functions as a ground for the antenna element 110.

In a case where the conductive plate 400 and the sensor support plate 102 are electrically connected to each other, a large loop is formed by a wireless communication circuit 106, the coaxial cable 109, the antenna element 110, and the sensor support plate 102. There is a possibility that this loop operates as an antenna, and becomes the source of the occurrence of noise or triggers a malfunction upon reception of disturbance noise. In the third embodiment, such an influence caused by the loop can be alleviated.

Next, a description is given of a method of adjusting the operating frequency band of the antenna element 110 in the third embodiment. The operating frequency band of the antenna element 110 may be adjusted by adjusting the size of the conductive plate 400. A current that has been generated as a result of supply of electrical signals to the antenna element 110 flows in the conductive plate 400, which functions as the ground for the antenna element 110. For this reason, the conductive plate 400 contributes to resonance of the antenna element 110. Therefore, the operating frequency band of the antenna element 110 can be adjusted by changing the size of the conductive plate 400. The conductive plate 400 may be larger than the antenna element 110 in a plan view relative to the conductive plate 400.

The operating frequency band of the antenna element 110 may be adjusted by adjusting the thickness (i.e., the length in the z-axis direction) and/or the material of the insulating member 401, in addition to or in place of adjusting the size of the conductive plate 400. Electromagnetic coupling occurs between the conductive plate 400 and the sensor support plate 102. The coupling amount of this electromagnetic coupling changes as a result of changing the thickness and/or the material of the insulating member 401. If the coupling amount of electromagnetic coupling changes, the operating frequency band of the antenna element 110 changes as well.

In order to increase the insulating property between the conductive plate 400 and the sensor support plate 102, it is sufficient to reduce the capacitance formed therebetween. In order to reduce this capacitance, it is sufficient to reduce the permittivity of the insulating member 401 or increase the thickness of the insulating member 401. However, an increase in the thickness of the insulating member 401 leads to an increase in the thickness of the radiation detection apparatus 100. In view of this, in some embodiments, the operating frequency band of the antenna element 110 may be adjusted by reducing the permittivity of the insulating member 401. For example, the insulating member 401 may be set to have a relative permittivity of 2 or less. For example, the insulating member 401 may be formed by a foamed material or the like. As a foamed material has a permittivity close to that of air, it increases the insulating property of the insulating member 401.

OTHER EMBODIMENTS

Figure 5:
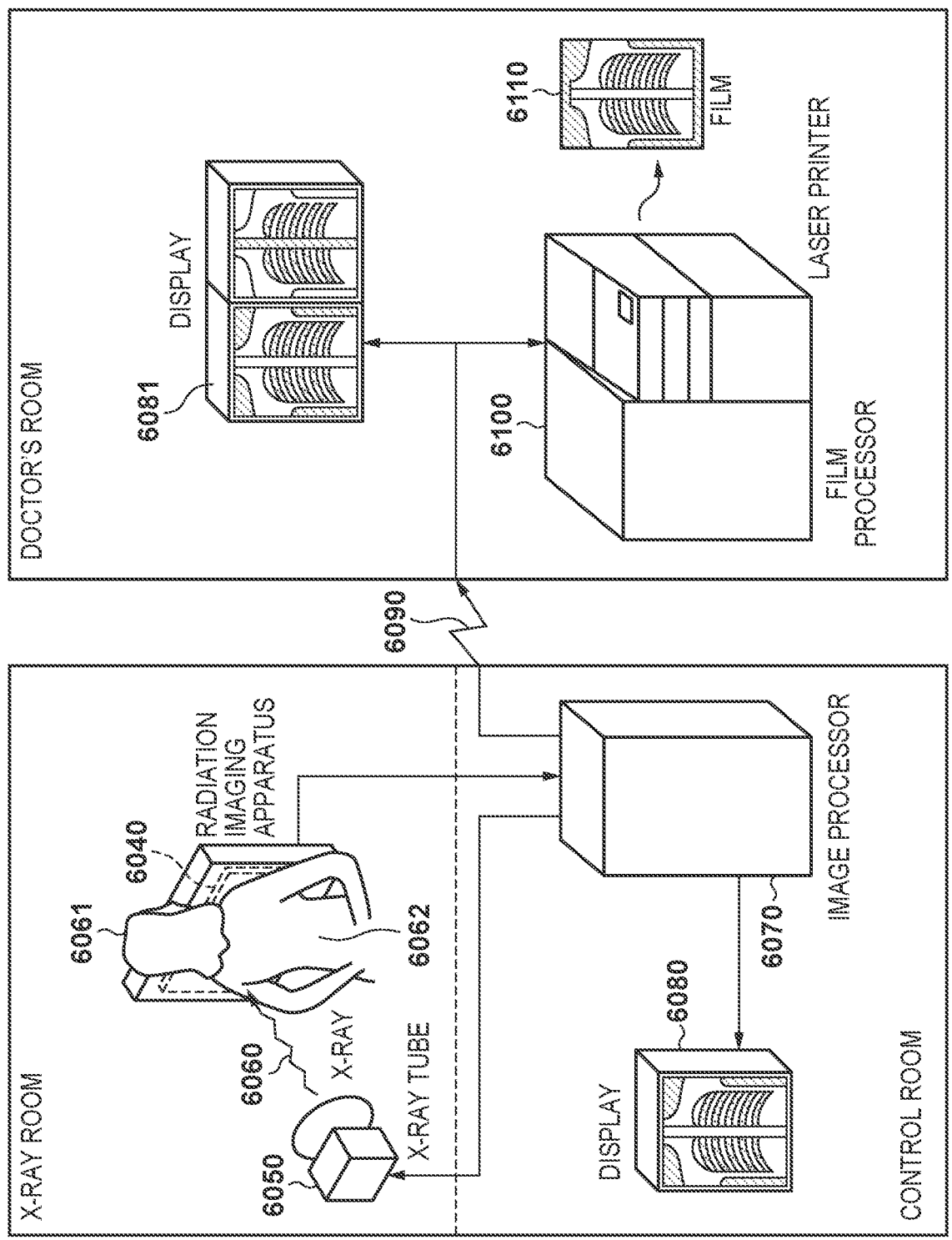
FIG. 5 is a schematic diagram for describing another embodiment.

FIG. 5 is a diagram showing an example in which the above-described radiation detection apparatus 100 has been applied to an X-ray diagnosis system (a radiation detection system). X-rays 6060, which represent radiation generated by an X-ray tube 6050 (a radiation source), are transmitted through a chest area 6062 of an examination subject or a patient 6061, and are made incident on a detection apparatus 6040. The detection apparatus 6040 may be the above-described radiation detection apparatus 100. The radiation detection apparatus 100 includes a scintillator that converts radiation into light. These incident X-rays include information of the inside of the body of the patient 6061. In correspondence with the incident X-rays, the scintillator emits light and photoelectrically converts the light, thereby obtaining electrical information. This information is converted into digital signals, undergoes image processing performed by an image processor 6070 that acts as a signal processing unit, and can be observed on a display 6080 that acts as a display unit in a control room. Note that the radiation detection system includes at least a radiation detection apparatus and a signal processing unit that processes signals from the radiation detection apparatus.

Also, this information can be transferred to a remote location by a transmission processing unit, such as a telephone line 6090; the information can be displayed on a display 6081 that acts as a display unit in a different place, such as a doctor's room, or stored in a recording unit, such as an optical disc, thereby enabling a doctor in a remote location to make a diagnosis. Furthermore, the information can also be recorded by a film processor 6100 that acts as a recording unit into a film 6110 that acts as a recording medium.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-200401, filed Dec. 9, 2021, which is hereby incorporated by reference herein in its entirety.

What is claimed is:

1. A radiation detection apparatus, comprising:
   a housing that includes an incidence surface and a back surface located on the opposite side of the incidence surface;
   a sensor panel within the housing, the sensor panel being configured to convert radiation incident from the incidence surface into an electrical signal;
   a conductive plate within the housing, and which extends in a direction intersecting with a normal to the incidence surface; and
   an antenna element within the housing, wherein
   the conductive plate is located between the sensor panel and the back surface,
   the antenna element is located between the conductive plate and the back surface in a region overlapping the conductive plate when viewed along a direction of incidence of the radiation,
   the antenna element includes a portion having a gap with the conductive plate and extending in the direction intersecting with the normal to the incidence surface, and
   the conductive plate and the antenna element are electrically connected.

2. The radiation detection apparatus according to claim 1, wherein the conductive plate supports the sensor panel.

3. The radiation detection apparatus according to claim 1, wherein the conductive plate is larger than the sensor panel in a plan view relative to the incidence surface.

4. The radiation detection apparatus according to claim 1, further comprising a support plate that supports the sensor panel, wherein
   the conductive plate is located between the support plate and the back surface.

5. The radiation detection apparatus according to claim 4, wherein the support plate is conductive, and is electrically connected to the conductive plate.

6. The radiation detection apparatus according to claim 4, further comprising an insulating member between the conductive plate and the support plate, wherein
the conductive plate and the support plate are electrically separated from each other by the insulating member.

7. The radiation detection apparatus according to claim 6, wherein the insulating member comprises a foamed material.

8. The radiation detection apparatus according to claim 1, wherein the housing comprises a conductor region and a transmissive region having a higher radio wave transmittance than the conductor region, and
at least a part of the antenna element overlaps the transmissive region in a plan view relative to the transmissive region.

9. The radiation detection apparatus according to claim 8, wherein a part of the antenna element overlaps the conductor region in a plan view relative to the transmissive region.

10. The radiation detection apparatus according to claim 1, further comprising:
a circuit board with a circuit installed thereon, the circuit being configured to perform wireless communication using the antenna element; and
a feed line including a first conductor and a second conductor that are electrically separated from each other, wherein
the circuit board is configured to supply an electrical signal to the antenna element via the first conductor of the feed line, and
the circuit board is configured to supply a ground potential to the conductive plate via the second conductor of the feed line.

11. The radiation detection apparatus according to claim 1, wherein the antenna element comprises an inverted-L antenna or an inverted-F antenna.

12. A radiation detection apparatus, comprising:
a housing that includes an incidence surface and a back surface located on the opposite side of the incidence surface;
a sensor panel within the housing, the sensor panel being configured to convert radiation incident from the incidence surface into an electrical signal;
a support plate that supports the sensor panel;
a conductive plate within the housing, and which has a surface extending across the normal of the incident surface; and
an antenna element within the housing, wherein
the support plate is located between the sensor panel and the back surface,
the conductive plate is located between the support plate and the back surface,
the antenna element is located between the conductive plate and the back surface in a region overlapping the conductive plate when viewed along a direction of incidence of the radiation,
the antenna element includes a portion having a gap with the conductive plate and extending in the direction intersecting with the normal to the incidence surface,
the conductive plate and the antenna element are electrically connected by bonding with a conductive sheet, and
the conductive plate and the supporting plate are separated by an insulating member.

* * * * *